United States Patent
Jeong et al.

(10) Patent No.: US 11,865,480 B2
(45) Date of Patent: Jan. 9, 2024

(54) NUCLEIC ACID PURIFICATION DEVICE AND NUCLEIC ACID PURIFICATION METHOD

(71) Applicants: ELECTRONICS AND TELECOMMUNICATIONS RESEARCH INSTITUTE, Daejeon (KR); Cancer Rop Co., Ltd., Seoul (KR)

(72) Inventors: Eun-Soo Jeong, Seoul (KR); Min Seon Kim, Seoul (KR); Kwang Hyo Chung, Daejeon (KR)

(73) Assignee: Electronics and Telecommunications Research Institute Cancer Rop Co., Ltd., Seoul (KR)

( * ) Notice: Subject to any disclaimer, the term of this patent is extended or adjusted under 35 U.S.C. 154(b) by 917 days.

(21) Appl. No.: 16/869,032

(22) Filed: May 7, 2020

(65) Prior Publication Data
US 2020/0353393 A1 Nov. 12, 2020

(30) Foreign Application Priority Data

May 7, 2019 (KR) .................. 10-2019-0053142
Mar. 3, 2020 (KR) .................. 10-2020-0026416

(51) Int. Cl.
| C12N 15/10 | (2006.01) |
| B01D 39/20 | (2006.01) |
| C12Q 1/6809 | (2018.01) |
| B01D 46/10 | (2006.01) |

(52) U.S. Cl.
CPC ....... *B01D 39/2055* (2013.01); *B01D 46/106* (2013.01); *C12N 15/1017* (2013.01); *C12Q 1/6809* (2013.01); *B01D 2201/043* (2013.01); *B01D 2201/4084* (2013.01); *B01D 2221/10* (2013.01)

(58) Field of Classification Search
CPC ............ C12N 15/1017; B01D 39/2055; B01D 2221/10; B01D 2239/0478; B01D 39/2065

See application file for complete search history.

(56) References Cited

U.S. PATENT DOCUMENTS

| 9,506,107 | B2 | 11/2016 | Erbacher et al. | |
| 2007/0175826 | A1* | 8/2007 | Iwata ................ | C12N 15/1017 436/178 |
| 2008/0053922 | A1* | 3/2008 | Honsinger, Jr. ...... | B01J 20/3212 210/508 |
| 2008/0275228 | A1* | 11/2008 | Mori ................. | C12N 15/1017 536/25.41 |
| 2012/0017763 | A1* | 1/2012 | Velpari .............. | B01D 39/163 28/107 |
| 2012/0156683 | A1 | 6/2012 | Baker | |

(Continued)

FOREIGN PATENT DOCUMENTS

| KR | 10-2002-0092778 A | 12/2002 |
| KR | 10-2009-0124923 A | 12/2009 |

(Continued)

*Primary Examiner* — Jonathan M Hurst
(74) *Attorney, Agent, or Firm* — Rabin & Berdo, P.C.

(57) ABSTRACT

A nucleic acid purification device according to the inventive concept includes an activated carbon fiber filter, wherein the activated carbon fiber filter includes an activated carbon fiber and a potassium compound coated on the surface of the activated carbon fiber.

5 Claims, 5 Drawing Sheets

(56) References Cited

U.S. PATENT DOCUMENTS

2016/0060681 A1    3/2016   Chung et al.
2019/0176155 A1    6/2019   Pyo et al.

FOREIGN PATENT DOCUMENTS

| KR | 10-2012-0107543 A | 10/2012 |
|----|-------------------|---------|
| KR | 10-1380909 B1 | 4/2014 |
| KR | 10-2014-0074407 A | 6/2014 |
| KR | 10-2018-0031089 A | 3/2018 |

\* cited by examiner

NUCLEIC ACID PURIFICATION DEVICE AND NUCLEIC ACID PURIFICATION METHOD

CROSS-REFERENCE TO RELATED APPLICATIONS

This U.S. non-provisional patent application claims priority under 35 U.S.C. § 119 of Korean Patent Application No. 10-2019-0053142, filed on May 7, 2019 and Korean Patent Application No. 10-2020-0026416, filed on Mar. 3, 2020, the entire contents of which are hereby incorporated by reference.

BACKGROUND

The present disclosure herein relates to a nucleic acid purification device and a nucleic acid purification method.

As genetic engineering has been advanced, a molecular diagnostic method using polymerase chain reaction (PCR), microarrays, next generation sequencing (NGS), or the like is developed, and thus diagnosis and prediction of various diseases may be performed based on genes. In addition, a method for efficiently extracting DNA from various samples is being required. As molecular diagnostic techniques have been advanced, PCR has been advanced so far as to be able to be performed within a short time of about 10 minutes, but it generally takes about 1 hour to perform an extraction and purification process of nucleic acids which is a pre-treatment process necessarily required for molecular diagnostics, and thus it is limited to use the molecular diagnostic technique in field diagnosis requiring rapidity.

SUMMARY

The present disclosure provides a nucleic acid purification device and a nucleic acid purification method which may make a simple process for purifying a nucleic acid and obtain a nucleic acid at a high yield.

An embodiment of the inventive concept provides a nucleic acid purification device including an activated carbon fiber filter, wherein the activated carbon fiber filter includes an activated carbon fiber and a potassium compound coated on the surface of the activated carbon fiber.

In an embodiment, the activated carbon fiber may have a specific surface area of 500-3,000 $m^2$/g.

In an embodiment, the activated carbon fiber may include pores having a diameter of 5-500 Å.

In an embodiment, the potassium compound may include at least one of potassium chloride (KCl), potassium iodide (KI), potassium hydroxide (KOH), potassium dihydrogen phosphite ($KH_2PO_3$), potassium hydrogen carbonate ($KHCO_3$), or potassium oxide ($K_2O$).

In an embodiment, the nucleic acid purification device further may include: a column tube having an inlet disposed at one end and an outlet disposed at the other end; a fixing ring which is disposed in the column tube and fixes the activated carbon fiber filter; and a filter paper in contact with the activated carbon fiber filter, wherein the activated carbon fiber filter may be disposed in the column tube, the fixing ring may be disposed closer to the inlet than the activated carbon fiber filter, and the filter paper may be disposed closer to the outlet than the activated carbon fiber filter.

An embodiment of the inventive concept provides a nucleic acid purification method including disrupting cells, and filtering the disrupted cells through an activated carbon fiber filter coated with a potassium compound.

In an embodiment, the disrupting of the cells may include adding an anionic surfactant to the cells.

In an embodiment, the filtering of the disrupted cells may include a centrifugation process.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Exemplary embodiments of the inventive concept will be described with reference to the accompanying drawings so as to sufficiently understand constitutions and effects of the present disclosure. The present disclosure may, however, be embodied in different forms with various changes and should not be construed as limited to the embodiments set forth herein. Rather, these embodiments are provided so that this disclosure will be thorough and complete, and will fully convey the scope of the present disclosure to those skilled in the art. In the accompanying drawings, the sizes of the components are exaggeratingly illustrated for the convenience of the description and the ratio of each component may be exaggerated or reduced.

Unless otherwise defined, all terms used in embodiments of the inventive concept have the same meaning as commonly understood by one of ordinary skill in the art to which the present disclosure belongs. Hereinafter, the present disclosure will be described in detail by explaining exemplary embodiments of the inventive concept with reference to the accompanying drawings.

Figure 1:
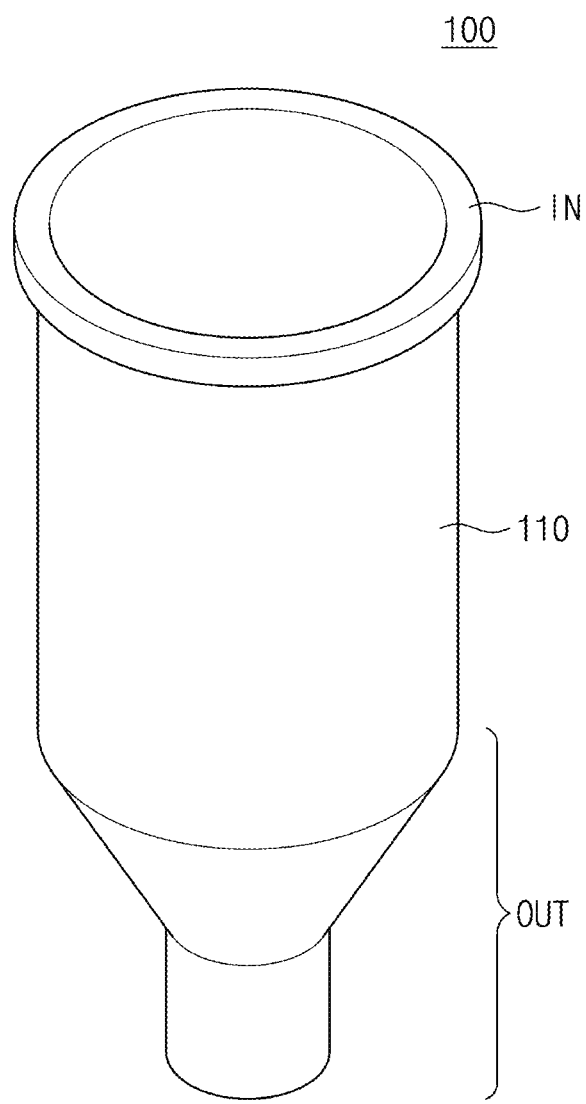
FIG. 1 is a perspective view of a nucleic acid purification device according to an embodiment of the inventive concept.
Figure 2:
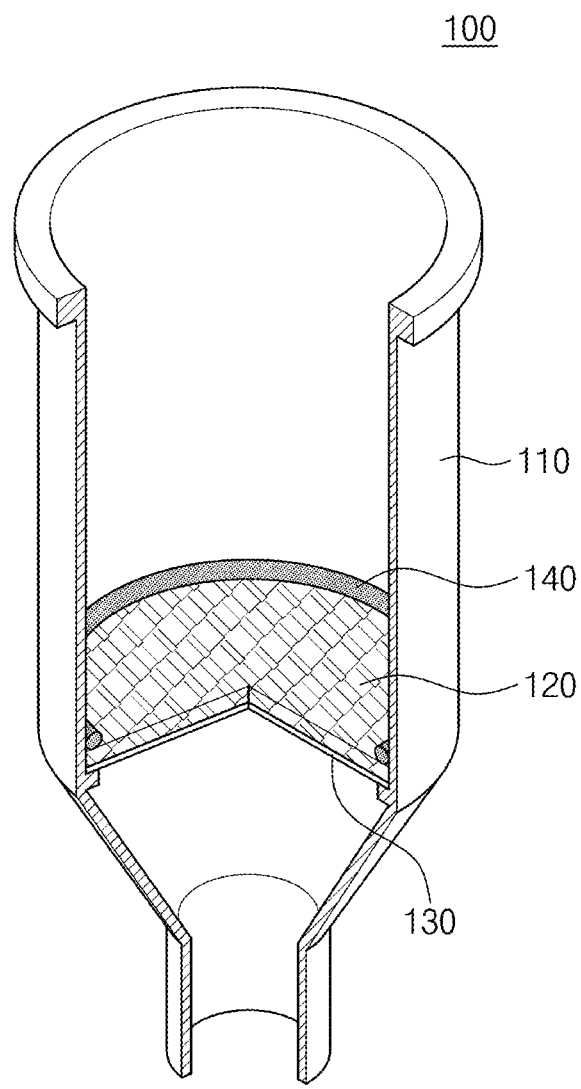
FIG. 2 is an inner perspective view of FIG. 1.

FIG. 1 is an outer perspective view of a nucleic acid purification device according to an embodiment of the inventive concept. FIG. 2 is an inner perspective view of FIG. 1.

Referring to FIGS. 1 and 2, a nucleic acid purification device 100 according to the inventive concept may include a column tube 110, a fixing ring 140, an activated carbon fiber filter 120, and a filter paper 130.

The column tube 110 may include an inlet IN into which a solution before purification is injected and an outlet OUT from which a solution after purification is discharged. The outlet OUT of the column tube 110 may be formed, for example, in a hopper shape so that the solution may be well discharged.

In the column tube 110, the filter paper 130 and the fixing ring 140 may be disposed with the activated carbon fiber filter 120 in-between. The shape of the inner diameter of the column tube 110 may be a circular shape, for example. The activated carbon fiber filter 120 may be disposed closer to the outlet OUT than the inlet IN. The fixing ring 140 may be disposed closer to the inlet IN than the carbon fiber filter 120, and the filter paper 130 may be disposed closer to the outlet OUT than the carbon fiber filter 120.

Figure 3:
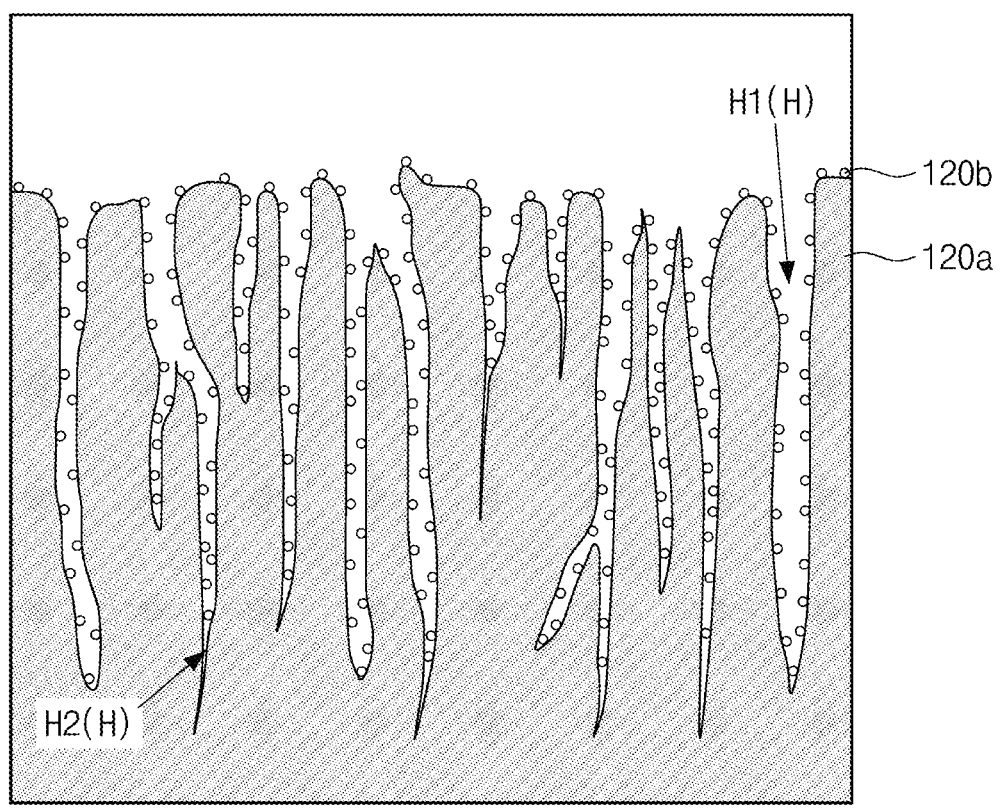
FIG. 3 is a schematic view of an activated carbon fiber filter.

FIG. 3 is a schematic view of an activated carbon fiber filter.

Referring to FIG. 3, the activated carbon fiber filter 120 may include an activated carbon fiber 120a and a potassium compound 120b coated on the activated carbon fiber 120a.

The activated carbon fiber 120a may be a fiber phase comprised of only carbon. Specifically, the activated carbon fiber 120a may be obtained by thermally decomposing rayon-based fibers, polyacrylonitrile (PAN)-based fibers, and pitch-based fibers (obtained from coal tar or petroleum heavy oil components as raw materials) with oxidizing gas such as chemical, water vapor, carbon dioxide, or oxygen.

The activated carbon fiber 120a may have, for example, a specific surface area of 500-3,000 $m^2/g$. The activated carbon fiber 120a may include a plurality of pores H.

The International Union Pure Applied Chemistry (IUPAC) divides pores into macropores, mesopores, and micropores according to the diameter size, and defines a pore having the diameter size of 20 Å or less as a micropore, a pore having the diameter size of 500 Å or less as a mesopore, and a pore having the diameter size of greater than 500 Å as a macropore.

The pores H of the activated carbon fiber 120a may have an average diameter of 5-500 Å. That is, the activated carbon fiber 120a may mainly include mesopores H1 and micropores H2. The short-stranded nucleic acid fragments, proteins, and organic solvents may be easily adsorbed in the mesopores H1 and the micropores H2.

In addition, since the macropores are less distributed, relatively large nucleic acids, such as plasmid DNA or genomic DNA (gDNA) may be minimally adsorbed.

The potassium compound 120b may be formed in a particle form on the surface of the activated carbon fiber 120a. The potassium compound 120b may include at least one of potassium chloride (KCl), potassium iodide (KI), potassium hydroxide (KOH), potassium dihydrogen phosphite ($KH_2PO_3$), potassium hydrogen carbonate ($KHCO_3$), or potassium oxide ($K_2O$).

The activated carbon fiber filter 120 may be formed by depositing the activated carbon fiber 120a with a solution in which the potassium compound 120b is dissolved and completely drying the wet activated carbon fiber at room temperature or in a high-temperature oven. In addition, some of the deposited solution in the activated carbon fiber 120b may be removed using centrifugation before the activated carbon fiber filter 120 is dried.

The fixing ring 140 may prevent separation of the activated carbon fiber filter 120. The filter paper 130 may prevent deformation of the activated carbon fiber filter 120 and filter relatively large particulate foreign materials contained in a solution to be filtered when centrifugation is carried out during filtration.

Figure 4:
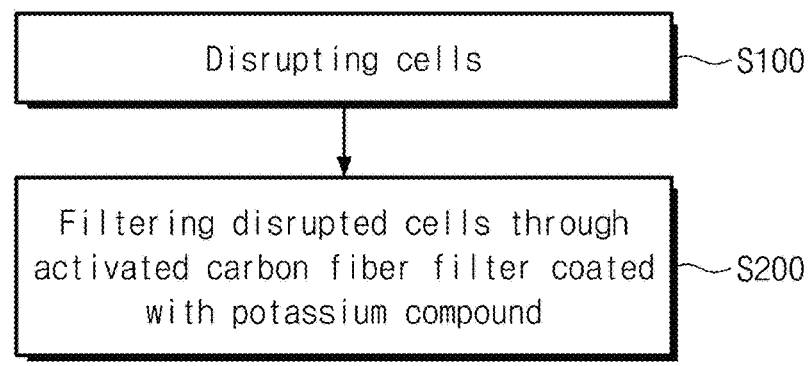
FIG. 4 is a flow chart illustrating a nucleic acid purification method according to an embodiment of the inventive concept.

FIG. 4 is a flow chart illustrating a nucleic acid purification method according to an embodiment of the inventive concept.

Referring to FIG. 4, the nucleic acid purification method may include disrupting cells S100, and filtering the disrupted cells through an activated carbon fiber filter coated with a potassium compound S200.

Before the disrupting the cells S100, the nucleic acid purification method may further include extracting the cells of interest. For example, in the case of extracting leukocytes in the blood, erythrocytes, platelets, and blood plasma other than the leukocytes may be removed. Nonionic surfactants are added in the blood, and erythrocytes, platelets, and blood plasma may be disrupted. Then, the supernatant may be removed by centrifugation, and the leukocytes collected on the bottom may be extracted.

The disrupting of the cells S100 may use at least one of physical methods or chemical methods. The physical methods may include a thermal lysis, an ultrasonic lysis, a high pressure homogenizer, a ball mill/bead mill, and a freeze-thaw.

The chemical methods may include adding a cell lysis solution including at least one of an anionic surfactant, an enzyme, or a salt into the cells. The anionic surfactant may include, for example, sodium lauryl sulfate (SLS) or sodium dodecyl sulfate (SDS). In some embodiments, the cell lysis solution is added to the leukocytes and subjected to heating and stirring step. Additionally, the disrupted cells (a solution state) may be diluted by adding distilled water or alcohol.

The disrupted cells may be filtered through the activated carbon fiber filter coated with the potassium compound (S200). The filtering step may be carried out in the nucleic acid purification device 100 as described with reference to FIGS. 1 to 3. The filtering step may include any one of a centrifugation process, a pressurized process, or a decompression process.

An anionic surfactant such as sodium dodecyl sulfate which is used to lyse cells may be bonded with $K^+$ ion coated on the surface of the activated carbon fiber to be condensed thereon. Therefore, the anionic surfactant may be then removed from the filtrate without a separate process. In addition, the micropores and the mesopores in the activated carbon fiber may be hardly observed in the filtrate since the adsorbing speed of nucleic acid fragments and an organic solvent is excellent. The activated carbon fiber may filter as large nucleic acids such as plasmid DNA or genomic DNA are minimally adsorbed since the macropores are less distributed in the activated carbon fiber. The observed nucleic acid may be, for example, any one selected from the group consisting of genomic DNA, RNA, plasmid DNA, mRNA, and rRNA.

EXAMPLE 1

Manufacture of Nucleic Acid Purification Device

An activated carbon fiber having a thickness of 1 mm was cut into a disk having a diameter of 7 mm. The disk-type activated carbon fiber 120a was immersed in 600 μL of a 100 mM potassium chloride solution.

After the wet activated carbon fiber 120a was taken out of the solution, the solution on the surface of the activated carbon fiber 120a was primarily removed by a 2 minute centrifugation at 12,000×G. The activated carbon fiber treated with the potassium chloride solution was thermally treated at 70° C. for 5 hours. The solvent of the potassium chloride solution was removed and the potassium chloride compound 120b was coated on the activated carbon fiber 120a to form the activated carbon fiber filter 120. Then, the activated carbon fiber filter 120 was placed on the filter paper 130 in the 7 mm column tube 110. The fixing ring matching the inner diameter of the column tube was then disposed on the activated carbon fiber filter.

EXAMPLE 2

Nucleic Acid Purification Method

Erythrocytes were disrupted by adding a nonionic surfactant to 200 µl of blood, centrifuged at 6,000×G for 1 minute to remove supernatant, and then leukocytes collected on the bottom were extracted.

35 µl of cell lysis solution containing sodium dodecyl sulfate was added to the extracted leukocytes, and the leukocytes were disrupted by heating and stirring at 56° C. for 10 minutes.

After adding 50 µl of distilled water, the resulting solution was placed in the nucleic acid separation device of Example 1, and DNA was purified by a 1 minute centrifugation at 12,000×G.

Figure 5:
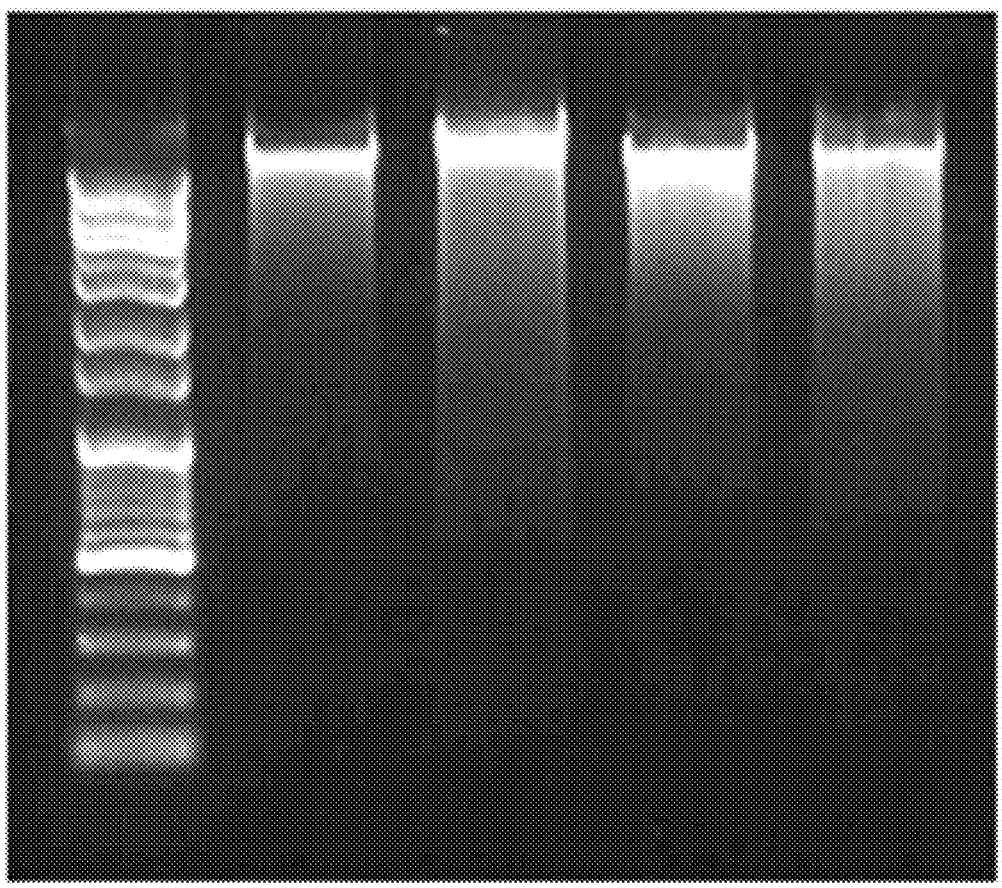
FIG. 5 is a photograph showing a comparison of a DNA sample extracted with the device and the method according to an embodiment of the inventive concept and DNA samples extracted with a commercial kit for extracting genomic DNA by performing electrophoresis analysis.

FIG. 5 is a photograph showing a comparison of a DNA sample extracted with the device and the method according to an embodiment of the inventive concept and DNA samples extracted with a commercial kit for extracting genomic DNA by performing electrophoresis analysis; and In FIG. 5, Experimental Example A is an electrophoresis diagram of the genomic DNA according to Example 2, Comparative Examples A and B are electrophoresis diagrams of the genomic DNA when using a commercial kit, and Comparative Example C is an electrophoresis diagram of the genomic DNA when using the activated carbon fiber but not coated with a potassium compound.

In the case of Comparative Examples A and B, disruption of the cells including three or more centrifugations, DNA adsorption, washing, and elution process were performed in order to extract genomic DNA.

Referring to FIG. 5, it was confirmed that, in Experimental Example A, the genomic DNA was purified similarly when using a commercial product. Therefore, since the method according to the present invention may be simply constituted with disrupting cells, filtering, and once centrifugation, DNA may be easily purified.

Figure 6:
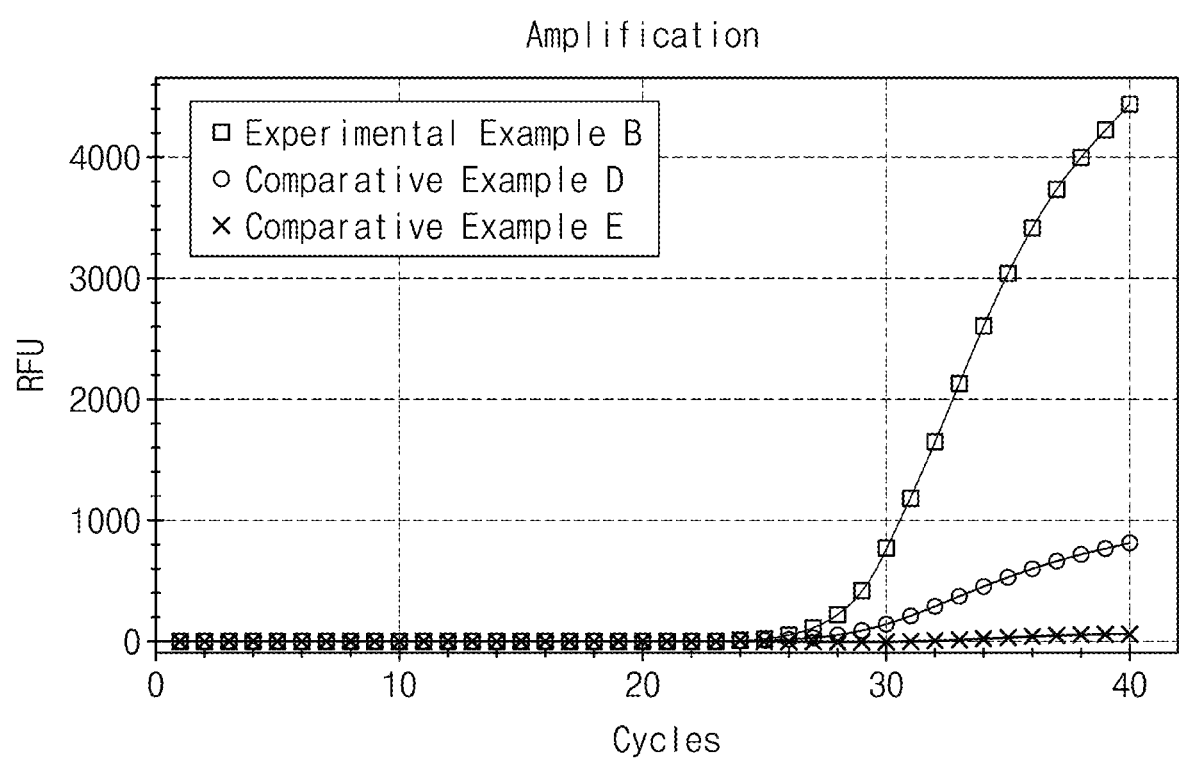
FIG. 6 is a graph showing the extent of nucleic acid amplification in the filtrate.

FIG. 6 is a graph showing the degree of amplification of nucleic acids in the filtrate.

Referring to FIG. 6, 35 µl of a cell lysis solution containing sodium dodecyl sulfate was added to leukocytes obtained by centrifuging 200 µl of blood for Experimental Example B, and the resultant solution was heated and stirred at 56° C. for 10 minutes. 50 µl of distilled water was added thereto, and the solution was put in the nucleic acid purification device (FIGS. 1 to 3) including the activated carbon fiber for nucleic acid purification prepared by the above method, DNA was purified by a 1 minute centrifugation at 12,000×G, and nucleic acid amplification was performed through real-time PCR.

Similarly, the amplification amount of DNA of the solution filtered with the activated carbon fiber not treated with potassium chloride was confirmed through real-time PCR.

In FIG. 6, it was confirmed that sodium dodecyl sulfate and impurities were sufficiently removed when real-time PCR was performed with a solution filtered through the active carbon fiber filter treated with potassium chloride, such that nucleic acid amplification was performed well (Experimental Example B). The solution filtered in the activated carbon fiber not treated with potassium chloride has an effect of removing impurities to some extent, but, seen from the form of an amplification curve, nucleic acid amplification was not sufficiently performed by real-time PCR due to the effects of remaining sodium dodecyl sulfate and impurities (Comparative Example D). The solution that was not subjected to the filtration process was not amplified by real-time PCR due to inhibition by sodium dodecyl sulfate and other impurities (Comparative Example E).

Using the nucleic acid purification device and the nucleic acid purification method according to the inventive concept allows rapid and effective purification of nucleic acids through a simple filtration process. The nucleic acid purification device according to the inventive concept includes an activated carbon fiber filter, wherein the activated carbon fiber filter may include an activated carbon fiber and a potassium compound coated on the surface of the activated carbon fiber. The activated carbon fiber may adsorb the others in cell lysates except for nucleic acids and the potassium compound may react with an anionic cell lysis solution to obtain high purification rate of nucleic acids in the filtrate.

Although the embodiments of the inventive concept are described with reference to the accompanying drawings, those with ordinary skill in the technical field to which the inventive concept pertains will understand that the present disclosure can be carried out in other specific forms without changing the technical idea or essential features. Thus, the above-described embodiments are to be considered illustrative and not restrictive to all aspects.

What is claimed is:

1. A nucleic acid purification device comprising an activated carbon fiber filter, wherein the activated carbon fiber filter comprises:
    an activated carbon fiber; and
    a potassium compound coated on the surface of the activated carbon fiber.
2. The nucleic acid purification device of claim 1, wherein the activated carbon fiber has a specific surface area of 500-3,000 m$^2$/g.
3. The nucleic acid purification device of claim 1, wherein the activated carbon fiber comprises pores having a diameter of 5-500 Å.
4. The nucleic acid purification device of claim 1, wherein the potassium compound 120b comprises at least one of potassium chloride (KCl), potassium iodide (KI), potassium hydroxide (KOH), potassium dihydrogen phosphite (KH$_2$PO$_3$), potassium hydrogen carbonate (KHCO$_3$), or potassium oxide (K$_2$O).
5. The nucleic acid purification device of claim 1, further comprising:
    a column tube having an inlet disposed at one end and an outlet disposed at the other end;
    a fixing ring which is disposed in the column tube and fixes the activated carbon fiber filter; and
    a filter paper in contact with the activated carbon fiber filter,
    wherein the activated carbon fiber filter is disposed in the column tube, the fixing ring is disposed closer to the inlet than the activated carbon fiber filter, and the filter paper is disposed closer to the outlet than the activated carbon fiber filter.

* * * * *